United States Patent [19]
Williams et al.

[11] Patent Number: 5,385,548
[45] Date of Patent: Jan. 31, 1995

[54] BALLOON CATHETER FOR RETROGRADE PERFUSION

[75] Inventors: Christopher R. Williams; Steven M. Gronsman; Roderick E. Briscoe, all of Grand Rapids, Mich.

[73] Assignee: DLP, Inc., Grand Rapids, Mich.

[21] Appl. No.: 51,023

[22] Filed: Apr. 22, 1993

[51] Int. Cl.⁶ .............................................. A61M 29/00
[52] U.S. Cl. ..................................... 604/96; 604/280; 600/16
[58] Field of Search ..................................... 600/16–18; 606/192, 194; 604/96, 97, 102, 280

[56] References Cited

U.S. PATENT DOCUMENTS

| | | |
|---|---|---|
| 3,985,601 | 10/1976 | Panagrossi . |
| 4,029,104 | 6/1977 | Kerber . |
| 4,188,954 | 2/1980 | Patel et al. . |
| 4,210,478 | 7/1980 | Shoney . |
| 4,290,428 | 9/1981 | Durand et al. . |
| 4,301,803 | 11/1981 | Handa et al. . |
| 4,535,757 | 8/1985 | Webster, Jr. . |
| 4,639,252 | 1/1987 | Kelly et al. . |
| 4,680,029 | 7/1987 | Ranford et al. ................... 604/280 |
| 4,689,041 | 8/1987 | Corday et al. . |
| 4,877,031 | 10/1989 | Conway et al. ................... 606/194 |
| 4,917,667 | 4/1990 | Jackson ............................ 604/96 |
| 4,927,412 | 5/1990 | Menasche . |
| 5,033,998 | 7/1991 | Corday et al. . |
| 5,197,952 | 3/1993 | Marcadis et al. ................. 604/96 |
| 5,324,260 | 6/1994 | O'Neill et al. ................... 604/96 |

FOREIGN PATENT DOCUMENTS

| | | |
|---|---|---|
| 1097881 | 1/1968 | United Kingdom . |
| 1097882 | 1/1968 | United Kingdom . |
| 1284701 | 8/1972 | United Kingdom . |
| 1414344 | 11/1975 | United Kingdom . |
| 1467976 | 3/1977 | United Kingdom . |
| 1477665 | 6/1977 | United Kingdom . |
| 1513918 | 6/1978 | United Kingdom . |

OTHER PUBLICATIONS

Brochure published in *The Annals of Thoracic Surgery*, vol. 19, No. 1, Jan. 1975 The brochure was produced by Sarns.

*Primary Examiner*—C. Fred Rosenbaum
*Assistant Examiner*—Connie Maglione
*Attorney, Agent, or Firm*—Varnum, Riddering, Schmidt & Howlett

[57] ABSTRACT

A catheter for retrograde perfusion of the heart through the coronary sinus, which has an infusion lumen for introducing perfusion liquid into the heart, a self inflating balloon, and a channeled flow tip at a distal end of the catheter for perfusing a cardioplegia solution into the coronary sinus.

13 Claims, 6 Drawing Sheets

BALLOON CATHETER FOR RETROGRADE PERFUSION

BACKGROUND OF THE INVENTION

1. Field of the Invention

This invention relates in general to cardioplegia catheters and, more particularly, to catheters having an improved self inflating balloon.

2. Description of Related Art

It has long been recognized in the field of cardiac surgery that it is necessary to interrupt the normal operation of the heart in order to provide the optimum surgical conditions. An arrested, flaccid heart is preferred during cardiac surgical procedures over a beating heart with blood flowing through it. In order to be able to efficiently perform cardiac surgery, it is often necessary to use cardiopulmonary-bypass techniques and to isolate the heart from its life giving blood supply.

A process known as cardioplegia, which literally means "heart stop," is used to stop the beating heart and, in some procedures, provide the necessary oxygen and fluid to the tissue of the heart. Cardioplegia can be administered in an antegrade manner (through arteries in the normal direction of blood flow), in a retrograde manner (through veins opposite the normal blood flow direction), or in a combination of retrograde and antegrade administration. Cardioplegia solutions, typically containing potassium, magnesium, procaine or a hypocalcemic solution, stop the heart by depolarizing cell membranes.

Retrograde cardioplegia is conventionally administered by inserting a balloon catheter within a heart vein, the coronary sinus, and forcing the cardioplegia solution through the infusion lumen of the catheter backwards through the coronary veins, a procedure commonly called perfusion. Catheters for retrograde coronary sinus perfusion (RCSP) can contain either a manually-inflating, or self-inflating balloon. A manually-inflatable balloon is inflated prior to starting the flow of cardioplegia solution. The balloon is typically filled with a fluid (normally air) from a syringe through an inflation lumen, either attached to the outer surface of the cannula body, or integral to the cannula body. A self-inflating balloon is in fluid communication with the infusion lumen of the catheter and is filled by a flow of cardioplegia solution through the infusion lumen into the balloon.

Typically, the distal end of the catheter is formed into a tip suitable for gently perfusing the coronary sinus. Such a flow tip should be relatively impervious to blockage by matter within the coronary sinus, or by the wall of the coronary sinus, lack sharp edges, and be formed of soft material to lessen the chances of injury to the coronary sinus. The flow tips on some previous designs have rounded distal ends to reduce trauma to the coronary sinus. Other previous designs incorporate multiple flow openings at the sides of the tip near its distal end, and sometimes at the center of the distal end of the tip, to reduce the chances that any one opening could become occluded during the perfusion procedure. However each opening creates a slight turbulence as it passes the perfusion fluid. Also, for the distal end of a flow tip to be truly rounded, the diameter of a central distal opening must generally be significantly less than the diameter of the perfusion lumen, thus increasing its potential for creating turbulence as it passes perfusion fluid.

SUMMARY OF THE INVENTION

The catheter according to the invention, incorporates a flow tip which overcomes the disadvantages of prior designs, and provides a gentle flow of perfusion fluid into the coronary sinus, and which is difficult if not impossible to occlude with known anatomical configurations of the coronary sinus.

A catheter for supplying liquid to an organ in a perfusion procedure, according to the invention, comprises a tubular catheter body having an interior lumen, a proximal end, and a distal end. A catheter entrance at the proximal end of the catheter body leads to the interior lumen. The catheter includes an inflatable balloon having proximal end and a distal end. The proximal end of the balloon encircles the catheter body at the distal end of the catheter body and the distal end of the balloon encircles a flow tip to define a balloon interior between the balloon and the catheter body and flow tip. At least one balloon entrance leads from the interior lumen to the balloon interior. The flow tip extends outwardly from the balloon and has at least one longitudinal flow channel extending from within the balloon interior to a point outside of the balloon interior and distal to the balloon. Each flow channel is open along a longitudinal side thereof, and the aggregate cross sectional area of the longitudinal channels is less than the aggregate cross sectional area of the balloon entrances.

Preferably, each flow channel extends to a distal end of the flow tip, is rounded in cross section and has substantially the same cross sectional shape over substantially its entire length. The greatest cross sectional diameter of each flow channel preferably exceeds the width of the opening along the channel's longitudinal side.

In one arrangement, the number of flow channels is three, and the flow channels are substantially equally spaced about the circumference of the flow tip.

A pressure monitoring lumen preferably extends from a point proximal of the balloon, to a point distal of the balloon, for putting the interior of the organ being perfused in pressure communication with the proximal end of the pressure monitoring lumen. The pressure monitoring lumen extends through the balloon and into one of the flow channels, and terminates within the flow channel at a point distal of the balloon.

In alternative aspect of the invention, a flow tip for passing a liquid from within an infusion lumen of a perfusion catheter to a point outside of the infusion lumen, the flow tip comprises an elongated member having at least one longitudinal flow channel. The flow channel is in fluid communication with the perfusion lumen of the catheter and open along a longitudinal side. The flow channel preferably extends to a distal end of the flow tip.

BRIEF DESCRIPTION OF THE DRAWINGS

The invention will now be described with reference to the drawings wherein.

DESCRIPTION OF THE PREFERRED EMBODIMENT

Figure 1:
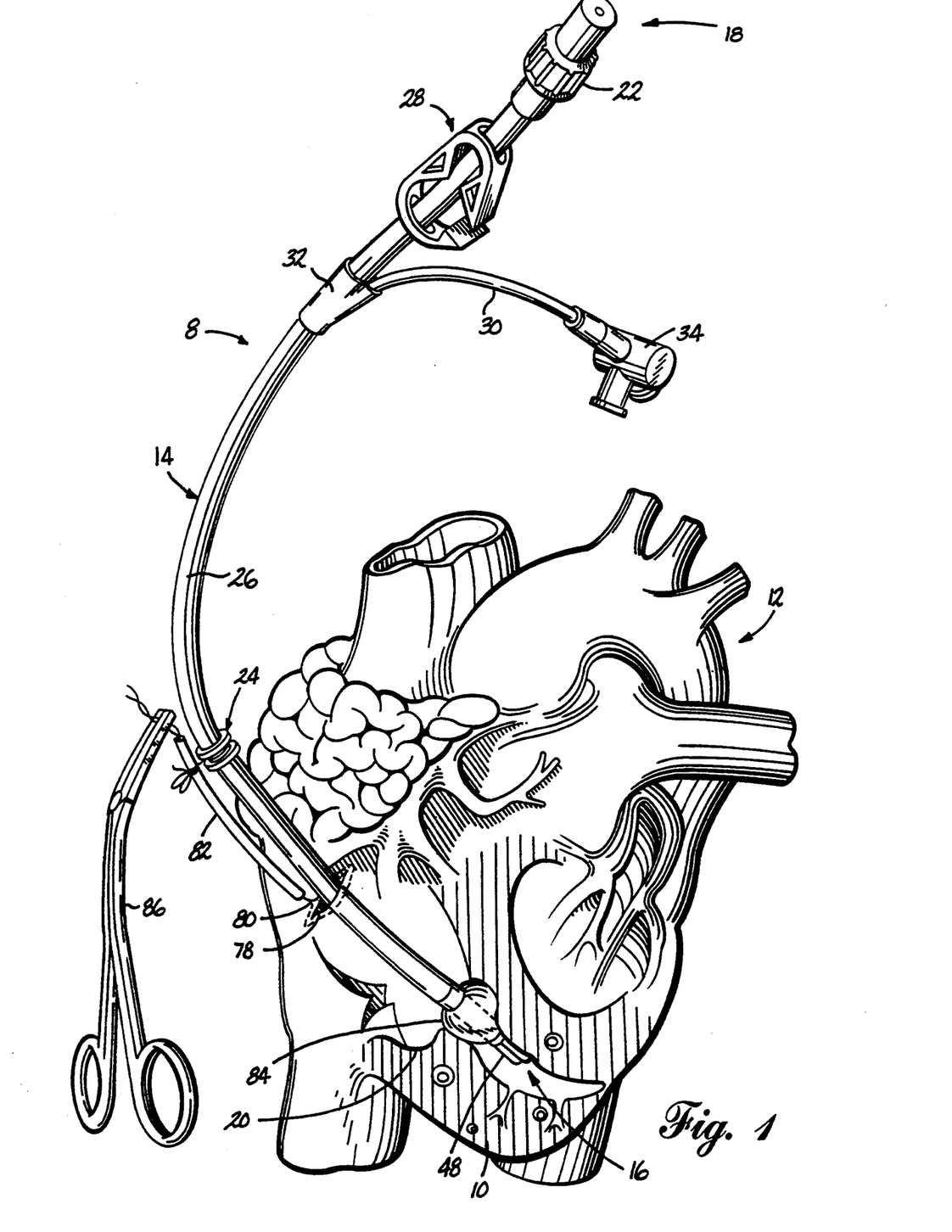
FIG. 1 is a partial sectional side elevational view of a self inflating balloon catheter according to the invention inserted into a coronary sinus vein.

Referring now the drawings and to FIG. 1 in particular, a catheter 8 for the introduction of fluid to a body organ is shown positioned in the coronary sinus vein 10 of a heart 12. The catheter 8 comprises a catheter body 14, having a distal end 16 and a proximal end 18. An inflatable balloon 20 attaches near the distal end 16 and a connector hub 22 attaches at the proximal end 18. A suture ring 24 mounts on the catheter body 14 and serves as an aid in securing attachment of the catheter 8 to the heart 12, as will be more fully described hereinafter.

Figure 2:
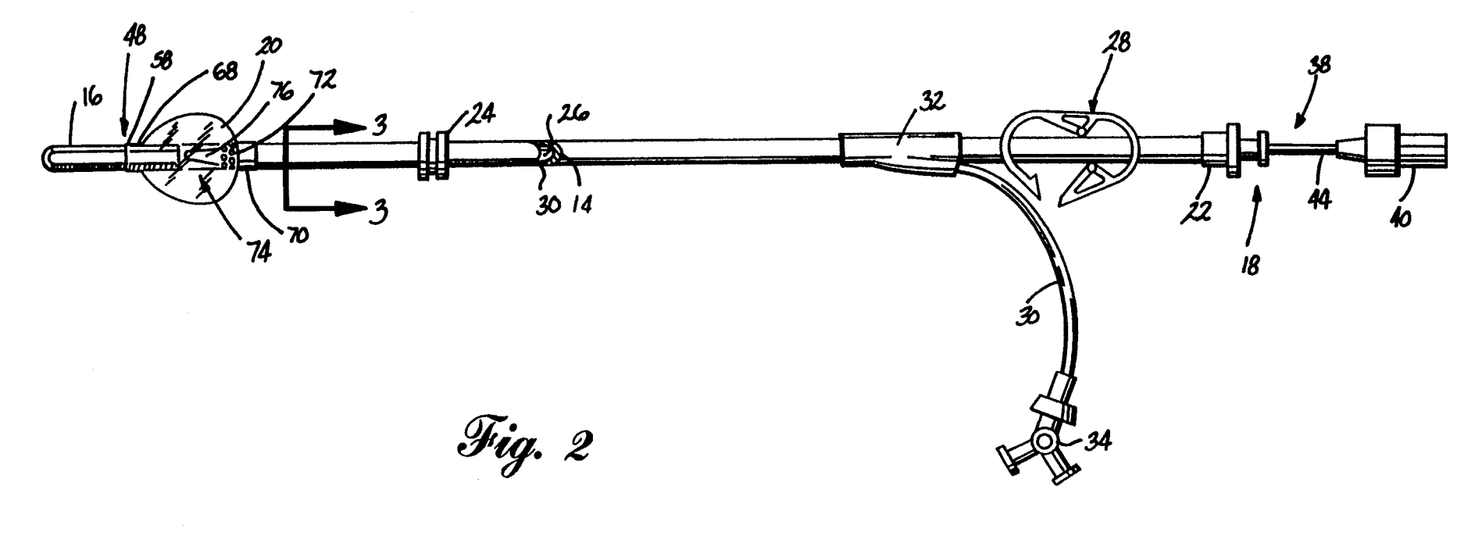
FIG. 2 is a side elevational view of the catheter of FIG. 1.
Figure 5:
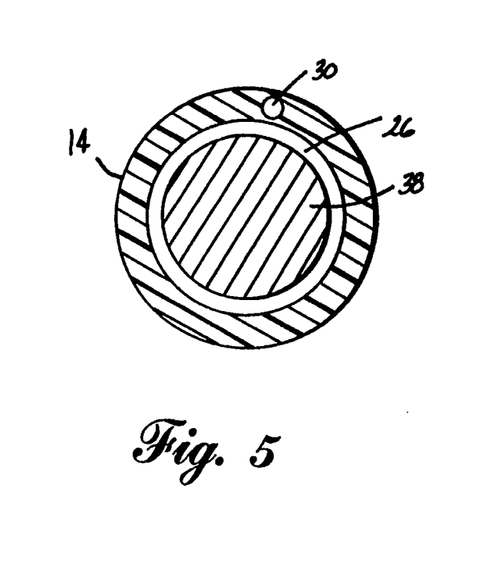
FIG. 5 is a sectional view of the catheter taken along lines 3—3 of FIG. 2.

Turning to FIG. 2, the catheter body 14 is preferably formed of a flexible plastic material suitable for introduction into the patient's body. As seen in section, the catheter body 14 is generally tubular in cross section, forming an infusion lumen 26 therethrough. (See also FIG. 5) The connector hub 22 is conventional and is of a suitable configuration for connecting the catheter body 14 to a source of cardioplegia solution. A clamping member 28 of conventional design can be mounted on the catheter body 14 adjacent and distal to the connector hub 22 for squeezing the catheter body 14 to occlude the infusion lumen 24.

A separate lumen 30, running over substantially the entire length of the catheter body 14, provides pressure monitoring capability. The pressure monitoring lumen 30 is preferably integrally molded into the catheter body 14 (See also FIG. 5) except for its proximal end which exits the catheter body 14 near its proximal end 18. A strain relief sleeve 32 made of an elastic material surrounds the catheter body 14 and pressure monitoring lumen 30 at the point the pressure monitoring lumen 30 exits the catheter body 14 to comprise a separate tubular body 30. An adhesive can be used to help seal the sleeve 32 to the catheter body 14 and pressure monitoring lumen 30.

A connector hub 34 mounts on the proximal end of the pressure monitoring lumen 30 and connects to a pressure monitoring device (not shown). The connector hub 34 may incorporate an integral three way valve so that the pressure monitoring lumen 30 can simultaneously connect to alternatively selectable pressure monitoring devices. The pressure monitoring lumen 30 extends to the distal end 16 of the catheter 8 so that the pressure monitoring device is in pressure communication with the inside of the coronary sinus 10.

Figure 3:
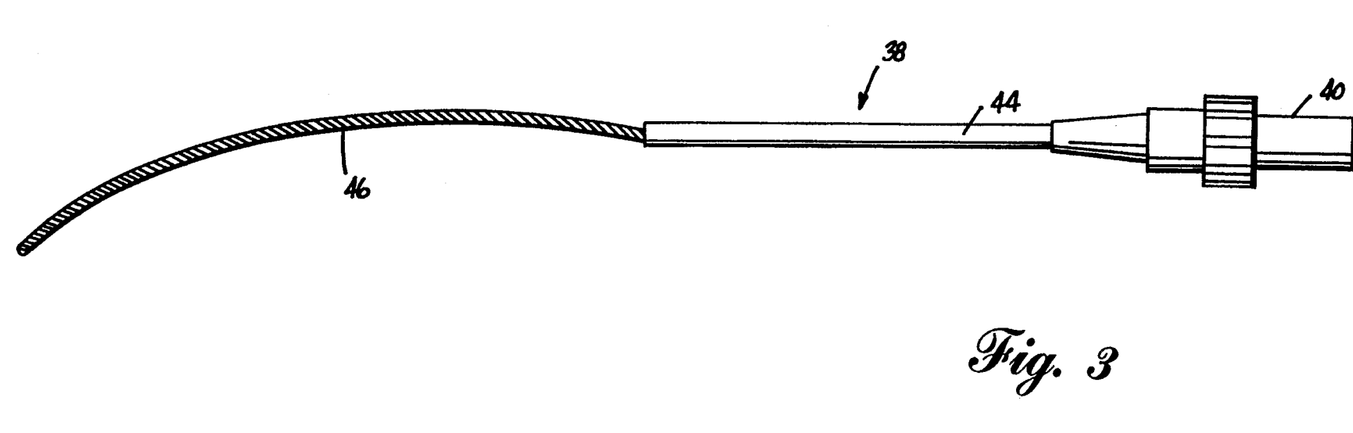
FIG. 3 is a side elevational view of a stylet for the catheter of FIG. 1.

The catheter body 14 is preferably very flexible and requires stiffening for proper insertion into the heart's coronary sinus vein 10. Typically, a stiff stylet 38 provides the necessary rigidity, and inserts coaxially into the catheter's infusion lumen 26 through the infusion lumen connector hub 22 at the proximal end 18 of the catheter 8. (See also FIG. 5 which shows a cross section of the catheter body 14, with the stylet 38 inserted into the infusion lumen 26.) The stylet 38 is removed from the catheter body 14 after the catheter 10 is properly positioned in the coronary sinus 10, and is shown partially retracted in FIG. 2. As shown in FIG. 3, the stylet 38 comprises a handle 40, and an elongated malleable wire 42 extending therefrom. A relatively rigid, although also malleable, sheath 44 typically extends from the handle 40 and coaxially receives the proximal third of the malleable wire 42. The sheath 44 provides added rigidity over the proximal portion of the stylet 38.

Figure 4:
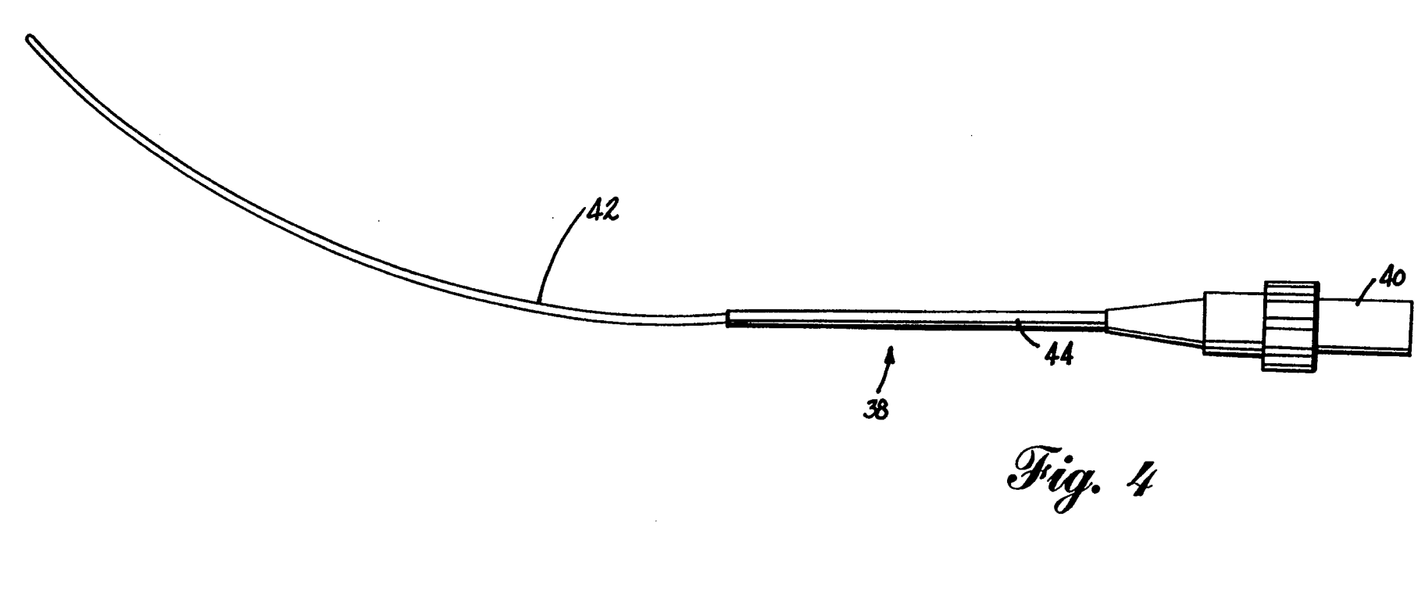
FIG. 4 is a side elevational view of an alternative stylet for the catheter of FIG. 1.

The malleable wire 42 is typically formed into a curved shape, similar to the curve of a hockey stick, by the surgeon prior to inserting the stylet into the catheter body 14. Thus, it is malleable for forming, yet rigid for proper stiffening of the catheter 10. Alternatively, the wire 42 may be preformed into an appropriate curve, which may be further customized by the individual surgeon. FIG. 4 shows an alternative stylet 38 having a malleable helical spring 46, in place of the malleable wire 42 of the stylet 38 of FIG. 3.

Figure 6:
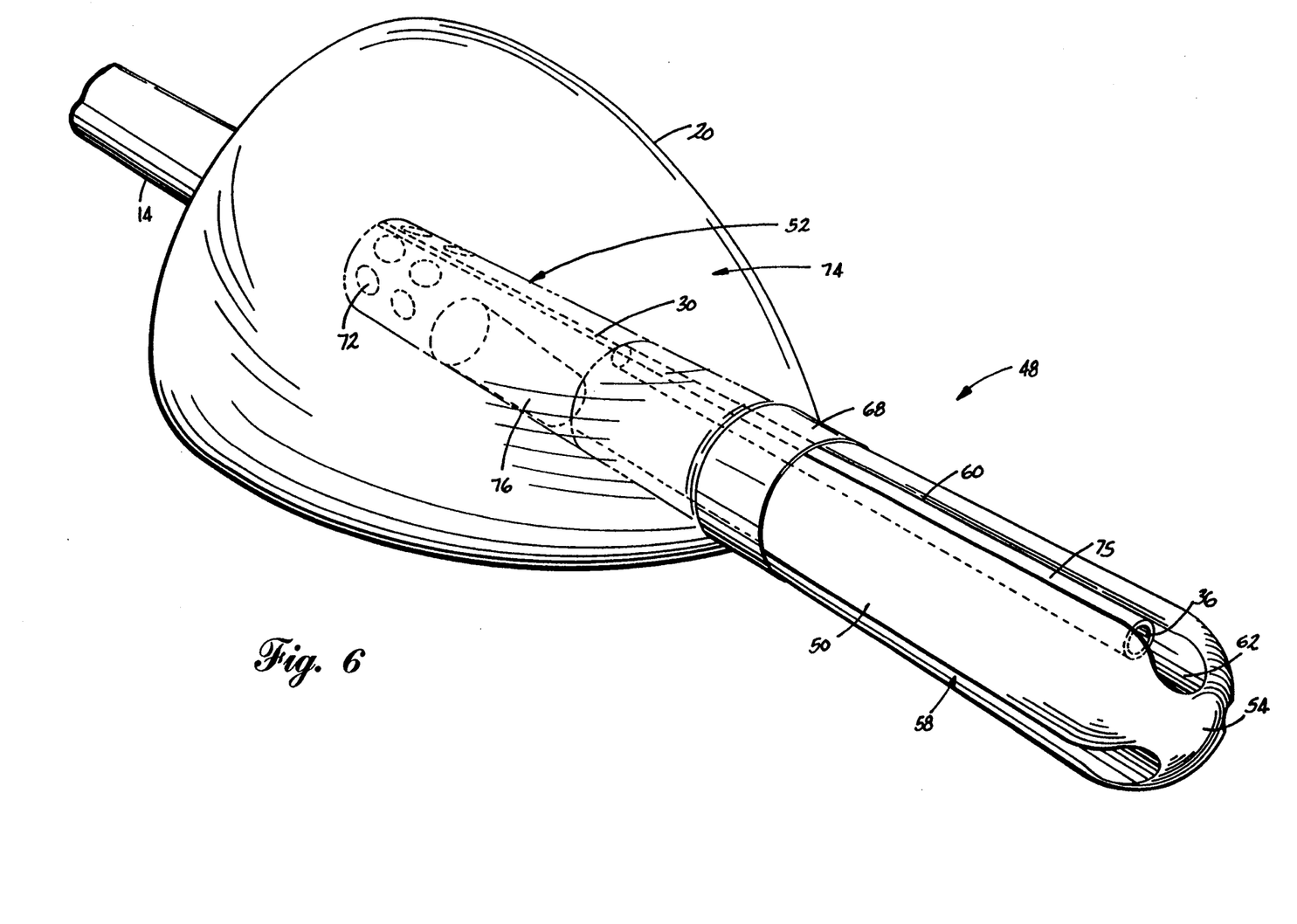
FIG. 6 is a perspective view of the balloon of the catheter of FIG. 1.

FIG. 6 shows a perspective view of the distal end 16 of the catheter 8. A flow tip 48 comprises a proximal base plug 52, and an elongated cylindrical body 50 which terminates in a rounded distal end 54. The infusion lumen 26 at a distal end 56 of the catheter body 14 receives the base plug 52, and the flow tip 48 extends axially therefrom. The diameter of the flow tip 48 preferably approximates the diameter of the catheter body 14.

Figure 7:
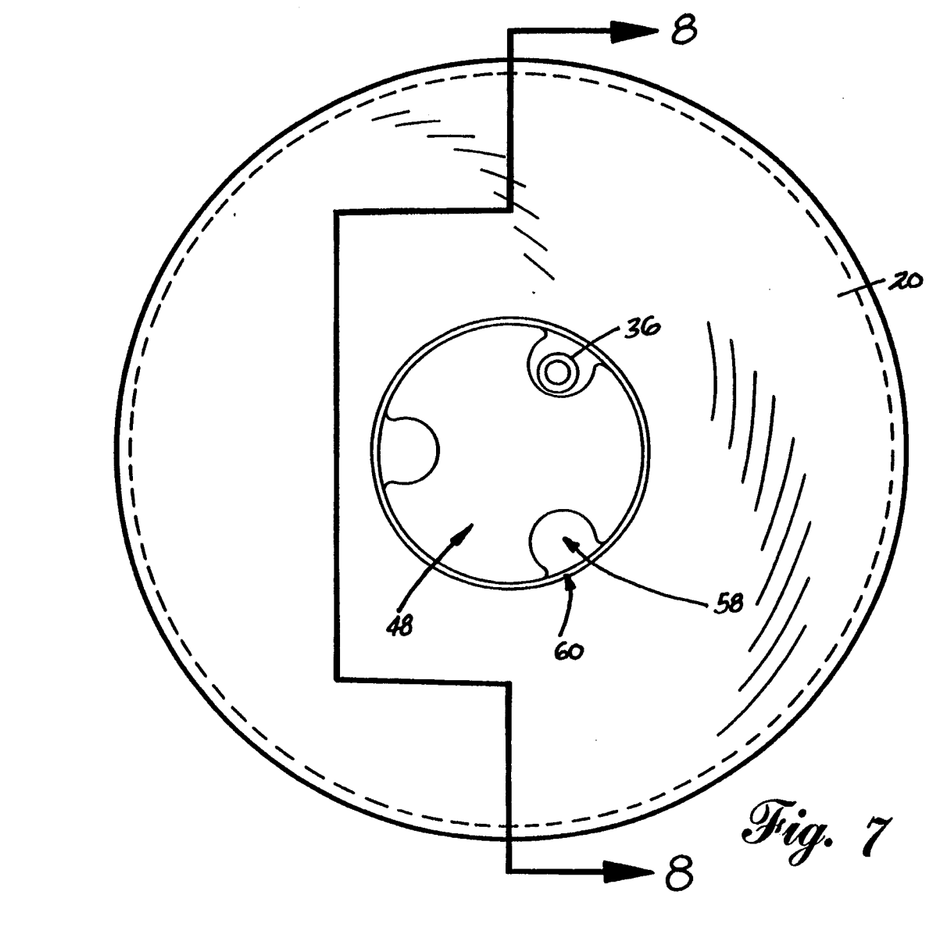
FIG. 7 is an end elevational view of a distal end of the catheter of FIG. 1.

Three open longitudinal flow channels 58 in the surface of the flow tip 48 each extend preferably the full length of the flow tip body 50 to its distal end 54. Preferably each flow channel 58 has a semi-circular cross section and is deeply recessed so that a longitudinal side opening 60 along the length of the flow channel 58 is smaller than the cross section of the flow channel 58 at its widest diameter. Each flow channel 58 also exits the distal end 54 of the flow tip 48 at a distal flow channel exit 62. FIG. 7 is an end view of the catheter's distal end 16, and more clearly shows the preferred cross section of the flow channels 58.

The flow channels 58 disperse the cardioplegia solution from the catheter 8 into the coronary sinus 10. The semi-enclosed cross sectional shape of the flow channels 58 directs flow through the distal flow channel exits 62, while allowing a portion of the flow to exit the channels through the longitudinal side exits 60. The channeled flow tip 48 provides a gentle, low shear, exit flow pattern for the cardioplegia fluid.

The design of the channeled flow tip 48, especially the combination of the elongated side exits 60 with the distal exits 62, prevents occlusion of the flow tip 48. The outflow path for cardioplegia fluid cannot be fully obstructed by any known anatomic configuration of the coronary sinus 10. To further reduce stress on the coronary sinus 10, the flow tip 48 is formed of a soft plastic, and its distal end 54 is rounded to a large radius, so as to make the flow tip 48 forgiving and easy to guide without damage to the endothelium (outer surface cells) of the wall of the coronary sinus 10.

Figure 8:
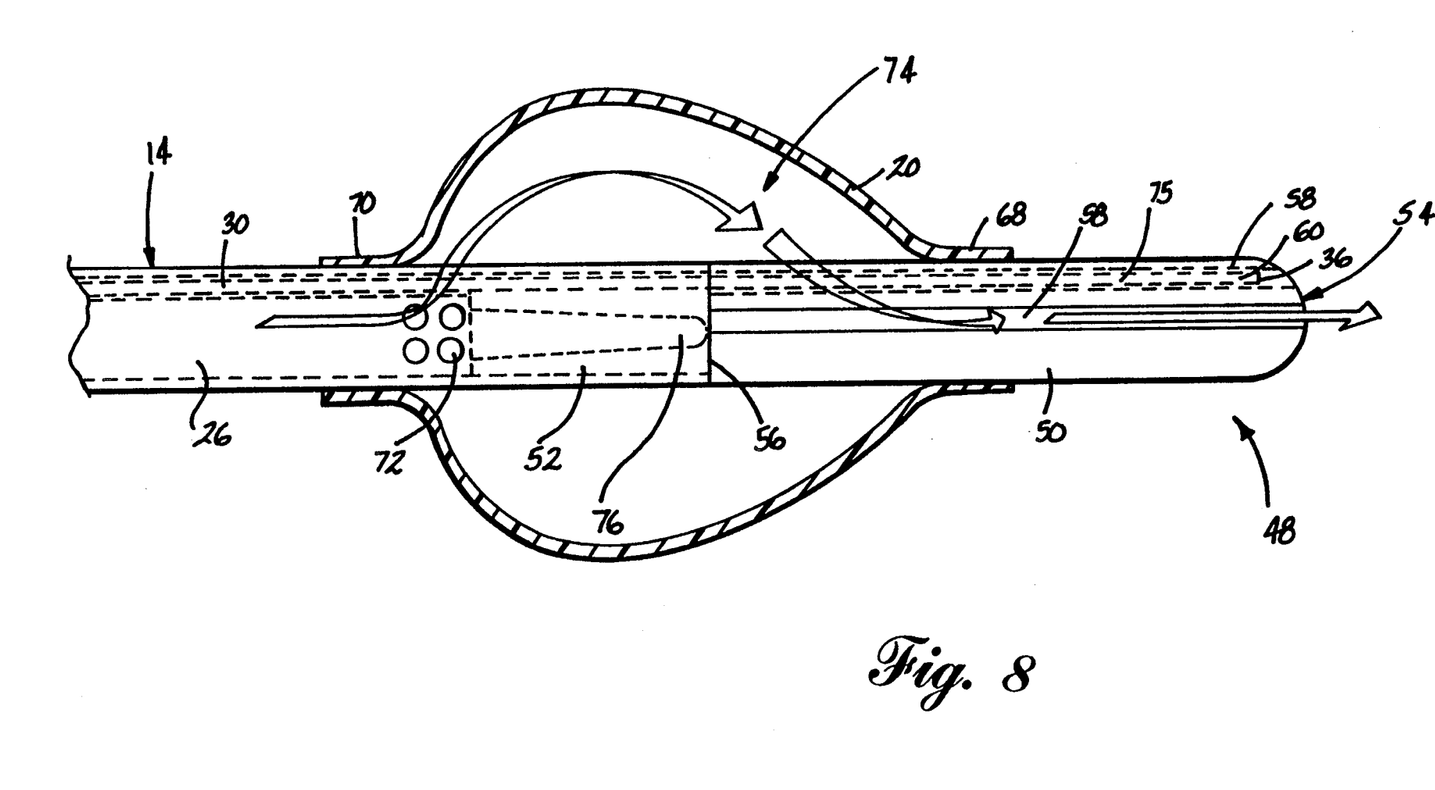
FIG. 8 is a sectional view of the balloon of the catheter taken along lines 8—8 of FIG. 7.

FIG. 8 illustrates the structure and operation of the self inflating balloon 20 and the flow tip 48. The pear shaped balloon 20 tapers gradually from its widest diameter to form a distal circular cuff 68, and tapers more quickly from its widest diameter to form a proximal circular cuff 70. The proximal cuff 70 coaxially receives the catheter body 14 and is attached thereto to form a fluid tight seal between the cuff 70 and the catheter body 14. The distal cuff 68 coaxially receives and attaches to the flow tip 48.

A plurality of radial holes 72 extend through the body of the catheter 14 from within the infusion lumen 26, proximal of the flow tip base plug 52, into an interior space 74 enclosed by the balloon 20. Thus the flow of cardioplegia fluid through the catheter 8 exits the infusion lumen 26 through the holes 72, enters the balloon interior 74, flows into the flow channels 58 and exits each flow channel 58 through its distal and side exits 62 and 60. The aggregate cross sectional area of the holes 72 filling the balloon interior 74 exceeds the aggregate cross sectional area of the flow channels 58 draining the balloon interior 74, providing a positive pressure within the balloon interior 74 to keep the balloon 20 inflated while the cardioplegia solution flows through the catheter 8.

The pressure monitoring lumen 30 extends through one of the open channels 58 by means of a urethane extension tube 75. (See also FIG. 7) The extension tube 75 extends from the flow tip body 50, where the pressure monitoring lumen 30 exits the flow tip body 50, through one of the flow channels 58, and terminates proximally adjacent the flow channel distal exit 62, to form the pressure lumen distal opening 36. The pressure monitoring equipment (not shown) is thus in pressure communication with the inside of the coronary sinus 10. Because the pressure lumen distal opening 36 is recessed into the flow channel 58, there is less chance of it becoming occluded by the wall of the coronary sinus 10.

Also note that a stylet well 76 can coaxially sink into the base plug 52 of the nozzle 48 for receiving the stylet 38 (not shown in FIG. 8), and providing additional reinforcement at the distal end 56 of the catheter body 14 where the stylet 38 impacts the base plug 52 of the nozzle 48.

Returning to FIG. 1, the catheter 8 according to the invention, is well suited for supplying cardioplegia solution to the heart muscle 12 during a surgical procedure. First, a small atriotomy (incision into the heart's atrium) 78 and purse string suture 80 are placed into the right atrial wall of the heart 12 and the free ends of the suture 80 are left to extend through a tubular tourniquet 82. The stylet 38 (FIGS. 3 or 4) is bent into a suitable hockey stick shaped curve and placed inside the infusion lumen 26 of the catheter 8 to provide rigidity.

The distal end 16 of the catheter 8, with the stylet 38 in place, is introduced into the right atrium 84 of the heart 12 through the atriotomy 78 and purse string suture 80 in the right atrial wall of the heart 12. The catheter body 14 is inserted into the coronary sinus 10 through its ostium (opening) 84 into the right atrium of the heart 12. The stylet 38 is then removed, the occluding clamp 28 on the catheter body 14 is closed, and the three way valve of the pressure monitoring lumen hub 34 is closed. The purse string 41 is tightened and the tourniquet 37 is clamped with a hemostat 86 to keep the purse string 80 closed. The tourniquet 82 is attached to the suture ring 24 on the catheter body 14 with additional suture material. The pressure monitoring lumen hub 34 and infusion lumen hub 22 are connected to their respective pressure monitor and cardioplegia sources and the lumens are purged of air in the standard fashion.

Once the catheter 8 is properly positioned within the coronary sinus 10 and connected to the pressure monitoring and cardioplegia supplying equipment, a suitable cardioplegia solution is introduced into the catheter 8 through its connector hub 22. The solution is under a slight pressure and passes through the infusion lumen 26 and exits the catheter body 14 through the holes 72, filling the balloon 20. The solution flows from the balloon 20 through the channels 58 into the coronary sinus 10 of the patient's heart 12.

The pressurized solution flows into the heart 12 tissue through the veins which normally empty into the coronary sinus 10 and arrests beating of the heart 12. Depending on the composition of the solution used, the solution can also provide necessary oxygen to the heart tissue to prevent damage thereto. The pressure of the cardioplegia solution within the coronary sinus is measured by the pressure monitoring equipment (not shown) connected to the pressure monitoring lumen 30. Constant pressure monitoring reduces the chances of developing high pressures within the coronary sinus 10 which can cause stress on the coronary sinus 10.

The balloon 20 serves two distinct functions in a cardioplegia perfusion process. First, the balloon 20 substantially fills the sinus ostium 84 thereby sealing the coronary sinus 10 from the right atrium of the heart 12. The pressurized cardioplegia solution introduced into the coronary sinus 10 through the catheter 8 is forced to flow backwards through the coronary sinus 10 into the veins which typically drain into the coronary sinus 10, and from there through the capillaries which serve the heart 12. Second, the balloon 20 engages the inside circumference of the coronary sinus 10 and sinus ostium 84 and retains the catheter 8 in place during the cardioplegia perfusion process.

While particular embodiments of the invention have been shown, it will be understood, of course, that the invention is not limited thereto since modifications can be made by those skilled in the art, particular in light of the foregoing teachings. Reasonable variation and modification are possible within the foregoing disclosure of the invention without departing from the spirit of the invention. For instance, the channeled design of the flow tip 48 is suitable for any perfusion catheter, and need not be limited to retrograde coronary sinus perfusion catheters.

The embodiments of the invention in which an exclusive property or privilege is claimed are defined as follows:

1. A catheter for supplying liquid to an organ in a perfusion procedure comprising;
   a tubular catheter body having an interior lumen, a proximal end, and a distal end;
   a catheter entrance at the proximal end of the catheter body leading to the interior lumen;
   an inflatable balloon having a proximal end and a distal end;
   a flow tip extending outwardly from distal end of the balloon;
   the proximal end of the balloon encircling the catheter body at the distal end of the catheter body and the distal end of the balloon encircling a flow tip to define a balloon interior between the balloon and the catheter body and flow tip;
   an entrance means comprising at least one passage from the interior lumen to the balloon interior; and
   the flow tip having a distal end and an exit means comprising at least one longitudinal flow channel extending from within the balloon interior to a point outside of the balloon interior and distal to the balloon, the at least one flow channel being open along a longitudinal side thereof forming an elongated longitudinal opening extending to the distal end of the flow tip.

2. A catheter according to claim 1 wherein the flow tip has a distal end away from the balloon and the at least one flow channel extends to the distal end of the flow tip.

3. A catheter according to claim 2 wherein the at least one flow channel is rounded in cross section and has substantially the same cross sectional shape over substantially its entire length.

4. A catheter according to claim 1 wherein the at least one flow channel communicates with the internal lumen only through the balloon interior.

5. A catheter for supplying liquid to an organ in a perfusion procedure comprising;
  a tubular catheter body having an interior lumen, a proximal end, and a distal end;
  a catheter entrance at the proximal end of the catheter body leading to the interior lumen;
  an inflatable balloon having a proximal end and a distal end;
  a flow tip extending outwardly from distal end of the balloon;
  the proximal end of the balloon encircling the catheter body at the distal end of the catheter body and the distal end of the balloon encircling the flow tip to define a balloon interior between the balloon and the catheter body and flow tip;
  an entrance means comprising at least one passage from the interior lumen to the balloon interior; and
  the flow tip having an exit means comprising three longitudinal flow channels substantially equally spaced about the circumference of the flow tip, each of the flow channels extending from within the balloon interior to a point outside of the balloon interior and distal to the balloon and being open along a longitudinal side thereof forming a longitudinal opening.

6. A catheter for supplying liquid to an organ in a perfusion procedure comprising;
  a tubular catheter body having an interior lumen, a proximal end, and a distal end;
  a catheter entrance at the proximal end of the catheter body leading to the interior lumen;
  an inflatable balloon having a proximal end and a distal end;
  a flow tip extending outwardly from distal end of the balloon;
  the proximal end of the balloon encircling the catheter body at the distal end of the catheter body and the distal end of the balloon encircling the flow tip to define a balloon interior between the balloon and the catheter body and flow tip;
  an entrance means comprising at least one passage from the interior lumen to the balloon interior;
  the flow tip having an exit means comprising more than one longitudinal flow channel extending from within the balloon interior to a point outside of the balloon interior and distal to the balloon, etch flow channel being open along a longitudinal side thereof forming a longitudinal opening; and
  a pressure monitoring lumen extending from a point proximal of the balloon, through the balloon and into one of the flow channels, and terminating within that flow channel at a point distal of the balloon, for putting the interior of the organ being perfused in pressure communication with a proximal end of the pressure monitoring lumen.

7. A catheter for supplying liquid to an organ in a perfusion procedure comprising;
  a tubular catheter body having an interior lumen, a proximal end, and a distal end;
  a catheter entrance at the proximal end of the catheter body leading to the interior lumen;
  an inflatable balloon having a proximal end and a distal end;
  a flow tip extending outwardly from distal end of the balloon;
  the proximal end of the balloon encircling the catheter body at the distal end of the catheter body and the distal end of the balloon encircling a flow tip to define a balloon interior between the balloon and the catheter body and flow tip;
  an entrance means comprising at least one passage from the interior lumen to the balloon interior;
  the flow tip having an exit means comprising at least one longitudinal flow channel extending from within the balloon interior to a point outside of the balloon interior and distal to the balloon, the at least one flow channel being open along a longitudinal side thereof forming a longitudinal opening; and
  the exit means having a cross sectional area and the entrance means having a cross sectional area, the cross sectional area of the exit means being less than the cross sectional area of the entrance means.

8. A catheter according to claim 7 further comprising a barrier separating the interior lumen and the at least one flow channel whereby the at least one flow channel communicates with the internal lumen only through the balloon interior.

9. A catheter for supplying liquid to an organ in a perfusion procedure comprising;
  a tubular catheter body having an interior lumen, a proximal end, and a distal end;
  a catheter entrance at the proximal end of the catheter body leading to the interior lumen;
  an inflatable balloon having a proximal end and a distal end;
  a flow tip extending outwardly from distal end of the balloon;
  the proximal end of the balloon encircling the catheter body at the distal end of the catheter body and the distal end of the balloon encircling the flow tip to define a balloon interior between the balloon and the catheter body and flow tip;
  an entrance means comprising at least one passage from the interior lumen to the balloon interior;
  the flow tip having an exit means comprising at least one longitudinal flow channel extending from within the balloon interior to a point outside of the balloon interior and distal to the balloon, the at least one flow channel being open along a longitudinal side thereof forming a longitudinal opening;
  the exit means having a cross sectional area the entrance means having a cross sectional area, the cross sectional area of the exit means being less than the cross sectional area of the entrance means and
  a barrier separating the interior lumen and the at least one flow channel whereby the at least one flow channel communicates with the internal lumen only through the balloon interior.

10. A catheter for supplying liquid to an organ in a perfusion procedure comprising;

a tubular catheter body having an interior lumen, a proximal end, and a distal end;

a catheter entrance at the proximal end of the catheter body leading to the interior lumen;

an inflatable balloon having a proximal end and a distal end;

a flow tip extending outwardly from distal end of the balloon;

the proximal end of the balloon encircling the catheter body at the distal end of the catheter body and the distal end of the balloon encircling the flow tip to define a balloon interior between the balloon and the catheter body and flow tip;

an entrance means comprising at least one passage from the interior lumen to the balloon interior; and the flow tip having an exit means comprising a plurality of longitudinal flow channels extending from within the balloon interior to a point outside of the balloon interior and distal to the balloon, each of the flow channels being open along a longitudinal side thereof forming a longitudinal opening.

11. A flow tip according to claim 10 and further comprising a longitudinally extending central core, and wherein the flow channels encircle the central core and are separated from each other by the central core.

12. A catheter for supplying liquid to an organ in a perfusion procedure comprising;

a tubular catheter body having an interior lumen, a proximal end, and a distal end;

a catheter entrance at the proximal end of the catheter body leading to the interior lumen;

an inflatable balloon having a proximal end and a distal end;

a flow tip extending outwardly from distal end of the balloon;

the proximal end of the balloon encircling the catheter body at the distal end of the catheter body and the distal end of the balloon encircling the flow tip to define a balloon interior between the balloon and the catheter body and flow tip;

an entrance means comprising at least one passage from the interior lumen to the balloon interior;

the flow tip having an exit means comprising at least one longitudinal flow channel extending from within the balloon interior to a point outside of the balloon interior and distal to the balloon, the at least one flow channel being open along a longitudinal side thereof forming a longitudinal opening; and the flow tip having a distal end away from the balloon, the flow tip distal end being rounded.

13. A flow tip for passing a liquid from a perfusion catheter having an inflatable balloon, an infusion lumen and an entrance means comprising a passage from the infusion lumen into the balloon, the flow tip comprising:

an elongated member having a distal end and a proximal end, the proximal end being adapted for receipt within a balloon of a perfusion catheter;

an exit means comprising a plurality of longitudinal flow channels extending to the distal end of the flow tip, each flow channel being open along a longitudinal side thereof; and a longitudinally extending central core, the flow channels encircling the central core and being separated from each other by the central core.

* * * * *

UNITED STATES PATENT AND TRADEMARK OFFICE
CERTIFICATE OF CORRECTION

PATENT NO. : 5,385,548
DATED : JANUARY 31, 1995
INVENTOR(S) : CHRISTOPHER R. WILLIAMS ET AL.

It is certified that error appears in the above-indentified patent and that said Letters Patent is hereby corrected as shown below:

Column 7, Claim 6, line 59:
    delete "etch" and insert therefor --each--.

Column 8, Claim 9, line 57:
    after "area" insert --and--.

Signed and Sealed this

Eighteenth Day of April, 1995

Attest:

BRUCE LEHMAN

Attesting Officer

Commissioner of Patents and Trademarks